United States Patent
Hayashida (10) Patent No.: US 8,045,676 B2
(45) Date of Patent: Oct. 25, 2011

(54) RADIATION IMAGING APPARATUS AND PROCESSING METHOD THEREFOR

(75) Inventor: Shinsuke Hayashida, Yokohama (JP)

(73) Assignee: Canon Kabushiki Kaisha, Tokyo (JP)

( * ) Notice: Subject to any disclaimer, the term of this patent is extended or adjusted under 35 U.S.C. 154(b) by 82 days.

(21) Appl. No.: 12/576,713

(22) Filed: Oct. 9, 2009

(65) Prior Publication Data
US 2010/0111256 A1 May 6, 2010

(30) Foreign Application Priority Data
Nov. 4, 2008 (JP) .................... 2008-283309

(51) Int. Cl.
*G01N 23/00* (2006.01)
(52) U.S. Cl. .............................. 378/7; 378/4
(58) Field of Classification Search .............. 378/4, 6, 378/7, 9
See application file for complete search history.

(56) References Cited

U.S. PATENT DOCUMENTS

2007/0253525 A1* 11/2007 Popescu ............................ 378/7
2009/0092222 A1* 4/2009 Okamoto et al. .................. 378/7

FOREIGN PATENT DOCUMENTS

JP 2004-121446 A 4/2004

* cited by examiner

*Primary Examiner* — Hoon Song
(74) *Attorney, Agent, or Firm* — Canon USA Inc IP Division (57) ABSTRACT

A radiation imaging apparatus acquires information on a scattered radiation distribution at each rotation angle preliminarily determined for a rotation unit, based on images respectively obtained from a first radiation detection sensor having no grid, and a second radiation detection sensor having a grid. Then, the radiation imaging apparatus corrects the image obtained from the second radiation detection sensor based on the information on the scattered radiation distribution so as to reduce influence of scattered radiation thereon. Next, the radiation imaging apparatus performs reconstruction processing based on the image corrected by the correction unit.

8 Claims, 9 Drawing Sheets

RADIATION IMAGING APPARATUS AND PROCESSING METHOD THEREFOR

BACKGROUND OF THE INVENTION

1. Field of the Invention

The present invention relates to a radiation imaging apparatus using a radiation detection sensor.

2. Description of the Related Art

In recent years, a two-dimensional flat type radiation detection sensor using semiconductor type photoelectric conversion elements has been developed. A cone-beam type computed tomography (CT) imaging apparatus, which uses such a radiation detection sensor and three-dimensional radiation, has been developed.

The cone-beam type CT imaging apparatus has a problem that an amount of generation of scattered radiation of X-rays is larger, as compared with a narrow-beam type CT imaging apparatus, which irradiates X-rays two-dimensionally.

On the other hand, Japanese Patent Application Laid-Open No. 2004-121446 discusses that when X-rays irradiated from a plurality of X-ray generation units are detected using X-ray detection units respectively facing the X-ray generation units, scattered radiation of X-rays irradiated from an X-ray generation unit and received by an X-ray detection unit that is not opposed to the X-ray generation unit is detected by the X-ray detection unit that is not opposed to the X-ray generation unit and corrected.

Japanese Patent Application Laid-Open No. 2004-121446 discusses that influence of X-rays, which is irradiated from an X-ray generation unit, on an X-ray detection unit that does not face the X-ray generation unit is suppressed. However, Japanese Patent Application Laid-Open No. 2004-121446 does not discuss technology for detecting a distribution of scattered radiation due to the influence of a subject and that is incident on a two-dimensional flat type X-ray detection sensor in a cone-beam type CT imaging apparatus.

SUMMARY OF THE INVENTION

The present invention is directed to a cone-beam type CT imaging apparatus capable of suppressing the amount of radiation with which the subject is exposed, acquiring a distribution of scattered radiation due to the influence of a subject, and correcting a reconstruction image to reduce the influence of the radiation.

According to an aspect of the present invention, a radiation imaging apparatus includes a first radiation detection sensor configured to detect radiation irradiated from a first radiation generation unit via no grid, a second radiation detection sensor configured to detect radiation irradiated from a second radiation generation unit via a grid, a rotation unit configured to rotate each of the first radiation detection sensor and the second radiation detection sensor relatively with respect to a subject, a correction unit configured to acquire information on a scattered radiation distribution based on images respectively obtained from the first radiation detection sensor and the second radiation detection sensor at each rotation angle preliminarily determined by the rotation unit and to correct the image obtained from the second radiation detection sensor based on the information on the scattered radiation distribution thereon, so as to reduce influence of scattered radiation thereon, and a reconstruction unit configured to perform reconstruction processing based on the image corrected by the correction unit.

Further features and aspects of the present invention will become apparent from the following detailed description of exemplary embodiments with reference to the attached drawings.

BRIEF DESCRIPTION OF THE DRAWINGS

The accompanying drawings, which are incorporated in and constitute a part of the specification, illustrate exemplary embodiments, features, and aspects of the invention and, together with the description, serve to explain the principles of the invention.

DESCRIPTION OF THE EMBODIMENTS

Various exemplary embodiments, features, and aspects of the invention will be described in detail below with reference to the drawings.

Figure 1:
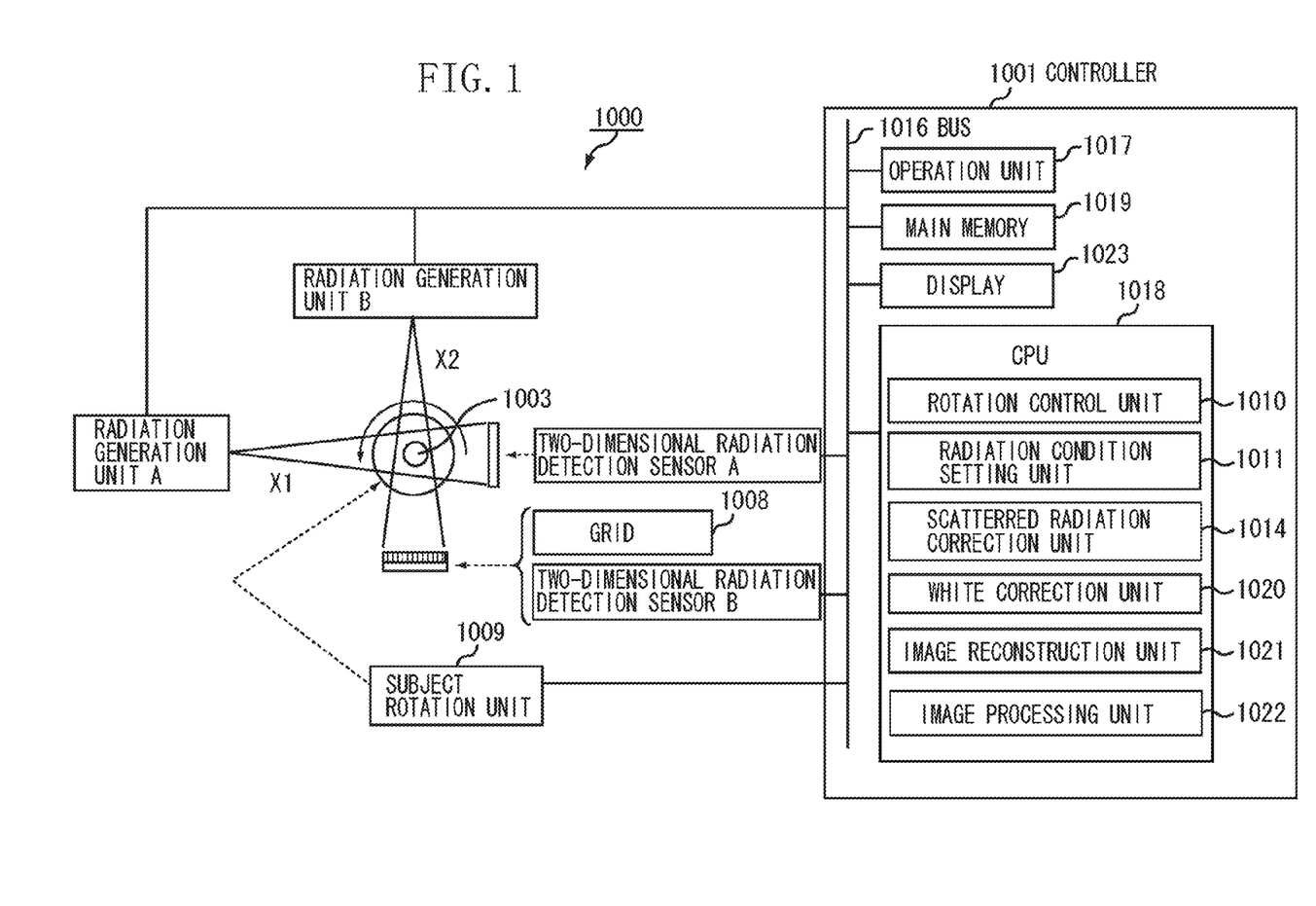
FIG. 1 illustrates a configuration of a radiation imaging apparatus according to a first exemplary embodiment of the present invention.

As illustrated in FIG. 1, a radiation imaging apparatus 1000 according to the present embodiment obtains a CT reconstruction image especially from radiation images continuously acquired while a subject is rotated relatively with respect to radiation generation units and two-dimensional radiation detection sensors (hereinafter sometimes referred to simply as two-dimensional radiation sensors) respectively facing the radiation generation units.

The radiation imaging apparatus 1000 includes a radiation generation unit A (first radiation generation unit), a radiation generation unit B (second radiation generation unit), two-dimensional radiation sensors A and B, a subject rotation unit 1009, and a controller 1001 for controlling these devices.

The two-dimensional radiation sensors A and B face the radiation generation units A and B that generate radiation, respectively, and detect radiation that has penetrated through the subject. The two-dimensional radiation sensor A, to which no grid is attached, is a first radiation detection sensor for detecting radiation via no grid. The two-dimensional radiation sensor B, to which a grid 1008 is attached, is a second radiation detection sensor for detecting radiation via the grid 1008.

The grid is a scattered radiation reduction member for reducing scattered radiation. The two-dimensional radiation sensor A is used to detect a scattered radiation distribution.

The two-dimensional radiation sensor B is used to acquire an image to be used to obtain a reconstruction image.

A subject rotation unit 1009 rotates a subject relatively with respect to the rotation generation units A and B, and the two-dimensional radiation sensors A and B. The controller 1001 includes an operation unit 1017, a main memory 1019, a display 1023 and a central processing unit (CPU) 1018.

The operation unit 1017 is an operation unit that is used to input various operations by a user, such as an instruction to execute radiation imaging, and various setting information to the radiation imaging apparatus 1000. The main memory 1019 includes a computer-readable memory, such as a read-only memory (ROM), which stores programs to be executed by the CPU 1018, and a random access memory (RAM) for temporarily storing programs, CT reconstruction image data, and the like.

The display 1023 is used to display a CT reconstruction image and the like, and includes a liquid crystal display (LCD).

The CPU 1018 performs, based on read programs, functions of a rotation control unit 1010, a radiation condition setting unit 1011, a scattered radiation correction unit 1014, a white correction unit 1020, and an image processing unit 1022.

The rotation control unit 1010 receives an imaging start request from the operation unit 1017 and rotates the subject at a preset speed. The radiation condition setting unit 1011 sets the intensity of radiation to be irradiated from the radiation generation units A and B in the main memory 1019, based on setting information input from the operation unit 1017.

The scattered radiation correction unit 1014 acquires a scattered radiation distribution in an image from image data detected by the two-dimensional radiation detection sensor B and corrects the image data detected by the sensor B, based on the scattered radiation distribution.

The white correction unit 1020 corrects sensitivity of image data detected by the two-dimensional radiation detection sensors A and B. More specifically, the sensitivity of output image data, when a subject is present, from the two-dimensional radiation detection sensors A and B, is corrected using correction image data obtained when radiation is irradiated to the two-dimensional detection sensors A and B without a subject. This correction processing is a known technique, and a description of this correction processing is omitted.

The image processing unit 1022 performs gradation processing and multiple frequency enhancement processing on image data output from the two-dimensional radiation detection sensor B. Thus, the image processing unit 1022 obtains a CT reconstruction image (tomographic image) based on a plurality of image data.

Figure 4:
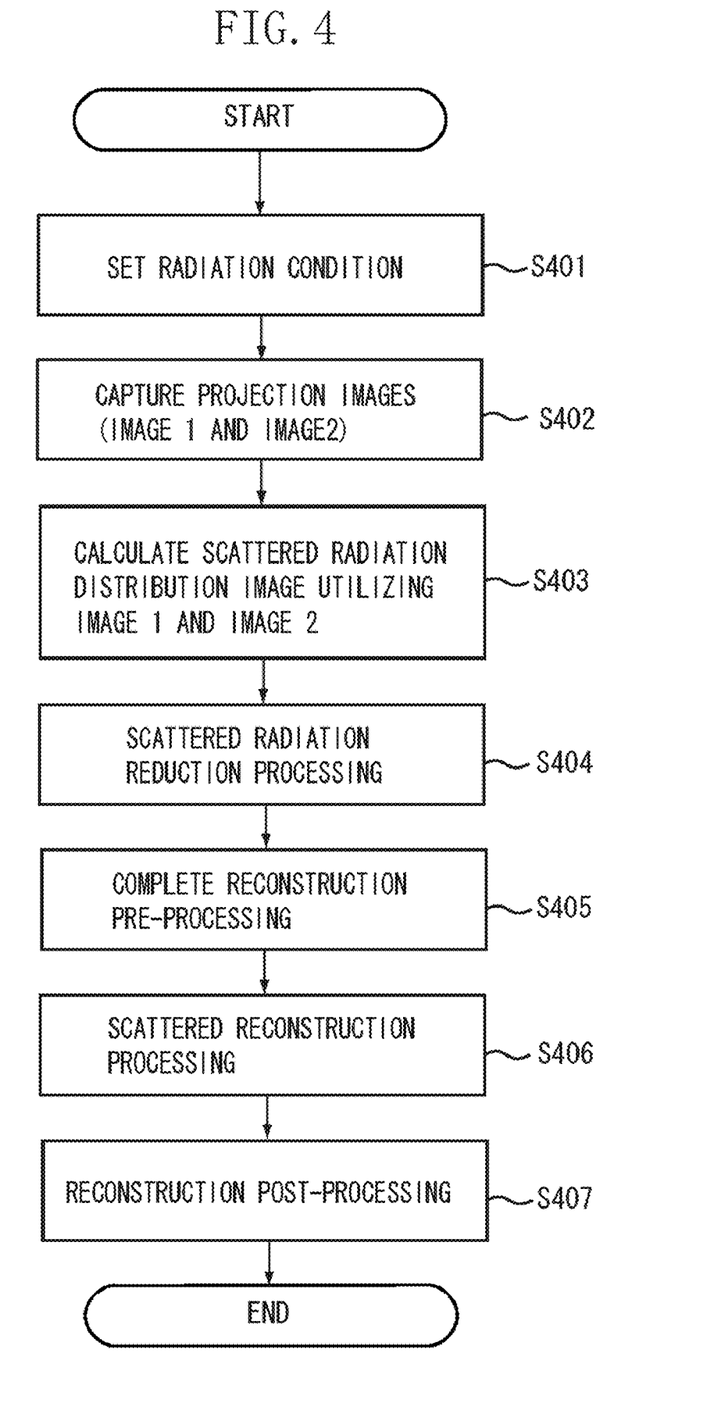
FIG. 4 is a flowchart illustrating processing performed by a controller.

FIG. 4 is a flowchart illustrating an operation of the controller 1001 according to the first exemplary embodiment of the present invention. The main memory 1019 stores data and processing programs, which are necessary for performing various processing in the CPU 1018 so as to implement an operation of the controller 1001, as a working memory (work memory) for the CPU 1018.

First, in step S401, the radiation condition setting unit 1011 sets a condition of radiation (intensity of radiation), which is input via the operation unit 1017, for generating radiation by the radiation generation units A and B in a state in which the subject is fixed to an appropriate place for the imaging apparatus.

In step S402, in response to an imaging request from the operation unit 1017, the rotation control unit 1010 drives and causes the subject rotation unit 1009 to perform an operation of rotating the subject. The radiation condition setting unit 1011 controls the radiation generation units A and B to generate radiation according to the preset condition.

Then, radiation that has penetrated through the subject is irradiated onto the two-dimensional radiation detection sensors A and B. Electric charge photoelectrically converted by the two-dimensional radiation detection sensors A and B is stored in the main memory 1019 as images.

In step S403, the scattered radiation correction unit 1014 obtains a scattered radiation distribution image using images obtained from the two-dimensional radiation detection sensors A and B. More specifically, among the images obtained from the two-dimensional radiation detection sensors A and B, an image 1 and an image 2 respectively obtained in the same radiation irradiating direction from the sensors A and B (when intervals for obtaining images are different between the sensor A and sensor B, closest images respectively obtained from the sensors A and B) are selected. Then, the level of a signal representing the image 1 is adjusted to that of a signal representing the image 2.

In addition, the scattered radiation correction unit 1014 subtracts a low-frequency region of the image, which is obtained from the two-dimensional radiation detection sensor B, from the image obtained from the two-dimensional radiation detection sensor A. Thus, a scattered radiation distribution image is obtained.

Although the scattered radiation distribution image depends on a person's shape (subject's shape), the scattered radiation distribution image varies gradually with respect to a rotation of the subject. More specifically, as experimentally known, it is useful to obtain a scattered radiation distribution image at each rotation angle interval of 18°. Consequently, in step S402, the number of times of imaging using the two-dimensional radiation detection sensor A can be set to be smaller than the number of times of imaging by the two-dimensional radiation detection sensor B.

Thus, it is better to set the intensity of radiation irradiated from the radiation generation unit B to be lower than that of radiation irradiated from the radiation generation unit A.

This is because of the fact that when an amount of generated radiation for detecting an amount of generation of scattered radiation is large, accuracy of the scattered radiation distribution is enhanced, whereas an amount of radiation, with which a subject is exposed, is increased. Scattered radiation is distributed in a low frequency region. Thus, even when pixel addition processing (binning processing) is performed for the two-dimensional radiation detection sensor B, sufficient correction accuracy can be maintained. Because the pixel addition processing can be performed, a scattered radiation distribution can be obtained even when the intensity of radiation is relatively low.

In step S404, the scattered radiation correction unit 1014 performs scattered radiation reduction processing on an image obtained from the two-dimensional radiation detection sensor B. More specifically, the scattered radiation correction unit 1014 subtracts the scattered radiation distribution image obtained in step S403 from the image obtained from the two-dimensional radiation detection sensor B.

In step S405, the image processing unit 1022 performs dark current correction processing, gain correction processing, and the like on the image subjected to the scattered radiation reduction processing in step S404.

In a flowchart illustrated in FIG. 4, a reconstruction pre-processing is performed in step S405 after the scattered radiation reduction processing is performed in step S404. However, this order can be changed. Particularly when a radiation detection sensor having a high dark current distribution or a radiation detection sensor having a sensitivity distribution which varies depending on pixels are used, it is desirable to calculate a scattered radiation distribution image after the dark current correction processing, the gain correction processing and the like are performed.

This is because it is difficult to distinguish variation in dark current and variation in sensitivity of each pixel, which vary depending on the two-dimensional detection sensors, from the scattered radiation distribution. Therefore, it is most desirable to perform the dark current correction processing and the gain correction processing before the processing performed in step S403.

In step S406, the image processing unit 1022 performs reconstruction processing based on a plurality of images processed in step S405. A reconstruction method, such as a Feldkamp method, which takes a cone angle into account, is desirable.

In step S407, the image processing unit 1022 performs gradation processing and multiple frequency enhancement processing on the reconstruction image obtained in step S406 as reconstruction post-processing to make the reconstruction image suited for being displayed on the display 1023.

Figure 5:
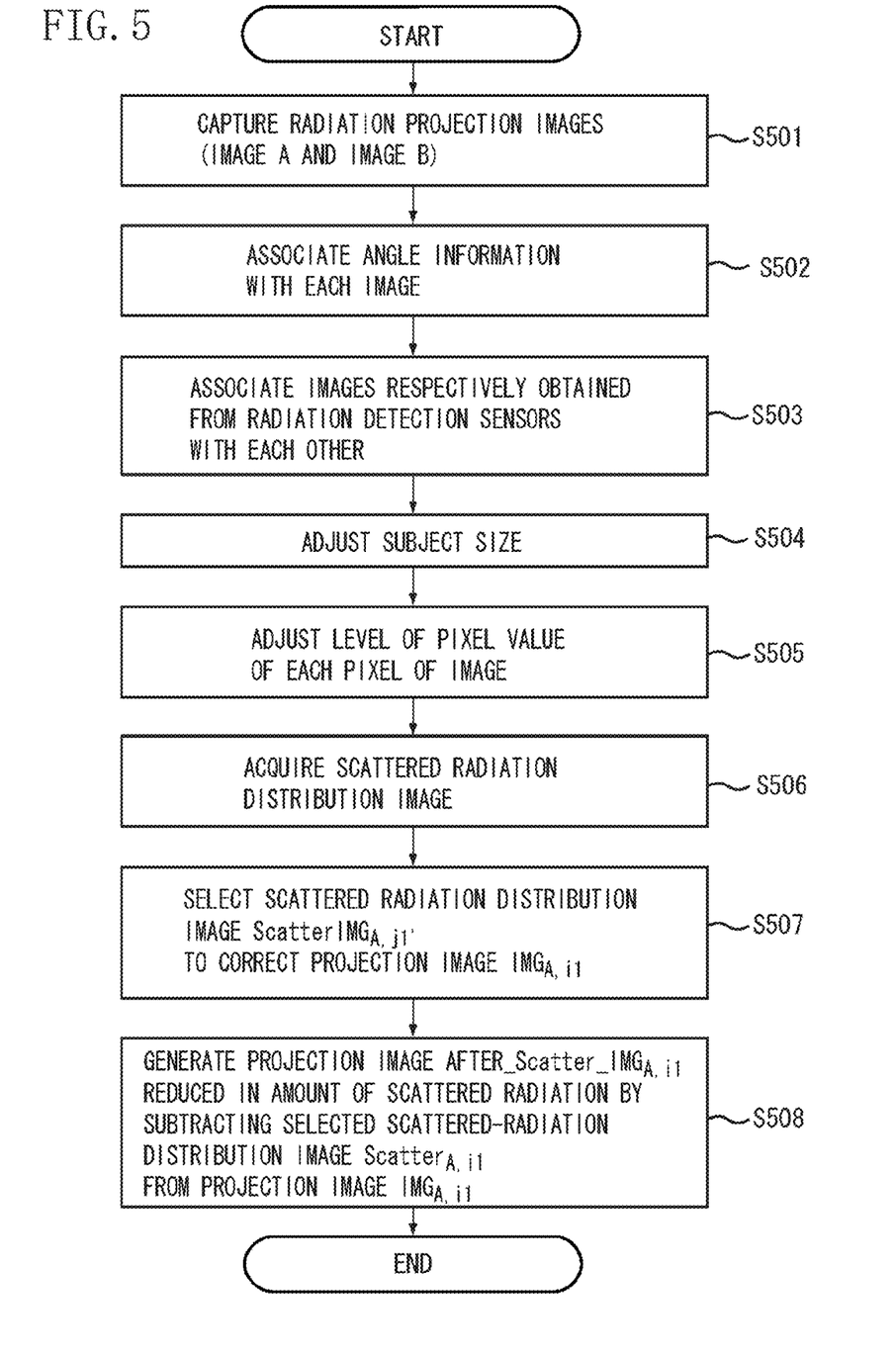
FIG. 5 is a flowchart illustrating an operation of acquiring a scattered radiation distribution image, which is performed by a scattered radiation correction unit.

FIG. 5 is a flowchart illustrating an operation for acquiring a scattered radiation distribution image performed by the scattered radiation correction unit 1014 of the CPU 1018. In other words, the flowchart illustrates details of step S403.

First, in step S501, the CPU 1018 stores images obtained from the two-dimensional radiation detection sensors A and B, respectively. It is assumed that an image A designated with "$IMG_{A, i1}$" is an image detected by the two-dimensional radiation detection sensor A, and that an image B designated with "$IMG_{B, i1}$" is an image detected by the two-dimensional radiation detection sensor B.

In step S502, a rotation angle with reference to a certain direction, at which each of the two-dimensional radiation detection sensors A and B captures an image, is associated by the CPU 1018 with a corresponding one of the image A "$IMG_{A, i1}$" and the image B "$IMG_{B, i1}$" obtained from the two-dimensional radiation detection sensors A and B, respectively.

This rotation angle information is obtained from a potentiometer included in the subject rotation unit 1009. According to the present exemplary embodiment, rotation angles at which the two-dimensional radiation detection sensors A and B obtain images are stored as a table in the main memory 1019.

It is assumed that the rotation angles at which the two-dimensional radiation detection sensor A obtains images are, e.g., 0°, 18°, 36°, . . . , and that the rotation angles at which the two-dimensional radiation detection sensor B obtains images are, e.g., 0°, 0.5°, 1.0°, 1.5°, . . . . The CPU 1018 controls the two-dimensional radiation detection sensors A and B such that the number of images obtained from the two-dimensional radiation detection sensor A is less than the number of images obtained from the two-dimensional radiation detection sensor B.

In step S503, the scattered radiation correction unit 1014 associates an image obtained from the two-dimensional radiation detection sensor B with an image obtained from the two-dimensional radiation detection sensor A, which is associated with a rotation angle close to a rotation angle of the image obtained from the two-dimensional radiation detection sensor B.

The number of images obtained from the two-dimensional detection sensor A is less than that of images obtained from the two-dimensional detection sensor B. Thus, a plurality of images obtained from the two-dimensional radiation detection sensor B may be associated with an image obtained from the two-dimensional radiation detection sensor A.

In step S504, the scattered radiation correction unit 1014 adjusts a size of a subject's image obtained from the two-dimensional radiation detection sensor A with that of an identical-subject's image obtained from the two-dimensional radiation detection sensor B at a rotation angle closest (or equal) to a rotation angle corresponding to the image obtained from the two-dimensional radiation detection sensor A. The reason for adjusting the sizes of the subject's images is that the distance from each of the radiation generation units A and B to an associated one of the two-dimensional radiation detection sensors and the distance from each of the radiation generation units A and B to the subject may differ.

When each enlargement factor of the subject images projected onto the two-dimensional radiation detection sensors A and B differs with each other, the operation of adjusting the sizes of the subject images indicated in the images obtained from the two-dimensional radiation detection sensors A and B is performed. More specifically, the enlargement factors respectively corresponding to the two-dimensional radiation detection sensors are obtained. The enlargement factor is defined as a ratio of the distance between the radiation generation unit A (B) and the detection surface of the two-dimensional radiation detection sensor A (B) to the distance between the radiation generation unit A (B) and the subject. The sizes of the subject's images respectively obtained from the two-dimensional radiation detection sensors A and B are adjusted to each other based on the enlargement factor or ratio.

In step S505, the scattered radiation correction unit 1014 adjusts pixel values of images respectively obtained from the two-dimensional radiation detection sensors A and B on which the adjustment of the sizes of the subject's images is performed. More specifically, in a state in which the subject is not present, the scattered radiation correction unit 1014 obtains in advance a multiplying factor, by which the pixel value corresponding to the image obtained from the two-dimensional radiation detection sensor B becomes equal to a pixel value corresponding to the image detected from the two-dimensional radiation detection sensor A. Then, the pixel value of each pixel of the image detected from the two-dimensional radiation detection sensor B is multiplied by the multiplying factor.

According to the present exemplary embodiment, when the two-dimensional radiation detection sensors A and B differ in resolution from each other, frequency processing and the like are performed to equalize resolutions as preparation processing for calculating an amount of scattered radiation.

In step S506, the scattered radiation correction unit 1014 obtains a scattered radiation distribution image by subtracting a low frequency region of the image obtained from the two-dimensional radiation detection sensor B from the image that is obtained from the two-dimensional radiation detection sensor A.

In step S507, the scattered radiation correction unit 1014 selects the scattered radiation distribution image for correcting each of projection images obtained from the two-dimensional radiation detection sensor B. The scattered radiation correction unit 1014 selects the scattered radiation distribution image, which is associated with the projection image obtained from the two-dimensional radiation detection sensor B and corresponds to the projection image obtained from the two-dimensional radiation detection sensor A.

In step S508, the scattered radiation correction unit 1014 obtains a projection image, which is reduced in an amount of scattered radiation, by subtracting the selected scattered radiation distribution image from the projection image obtained from the two-dimensional radiation detection sensor B.

This processing results in reduction in degree of image unevenness, in the reconstructed image, due to the influence of the scattered radiation.

Figure 6:
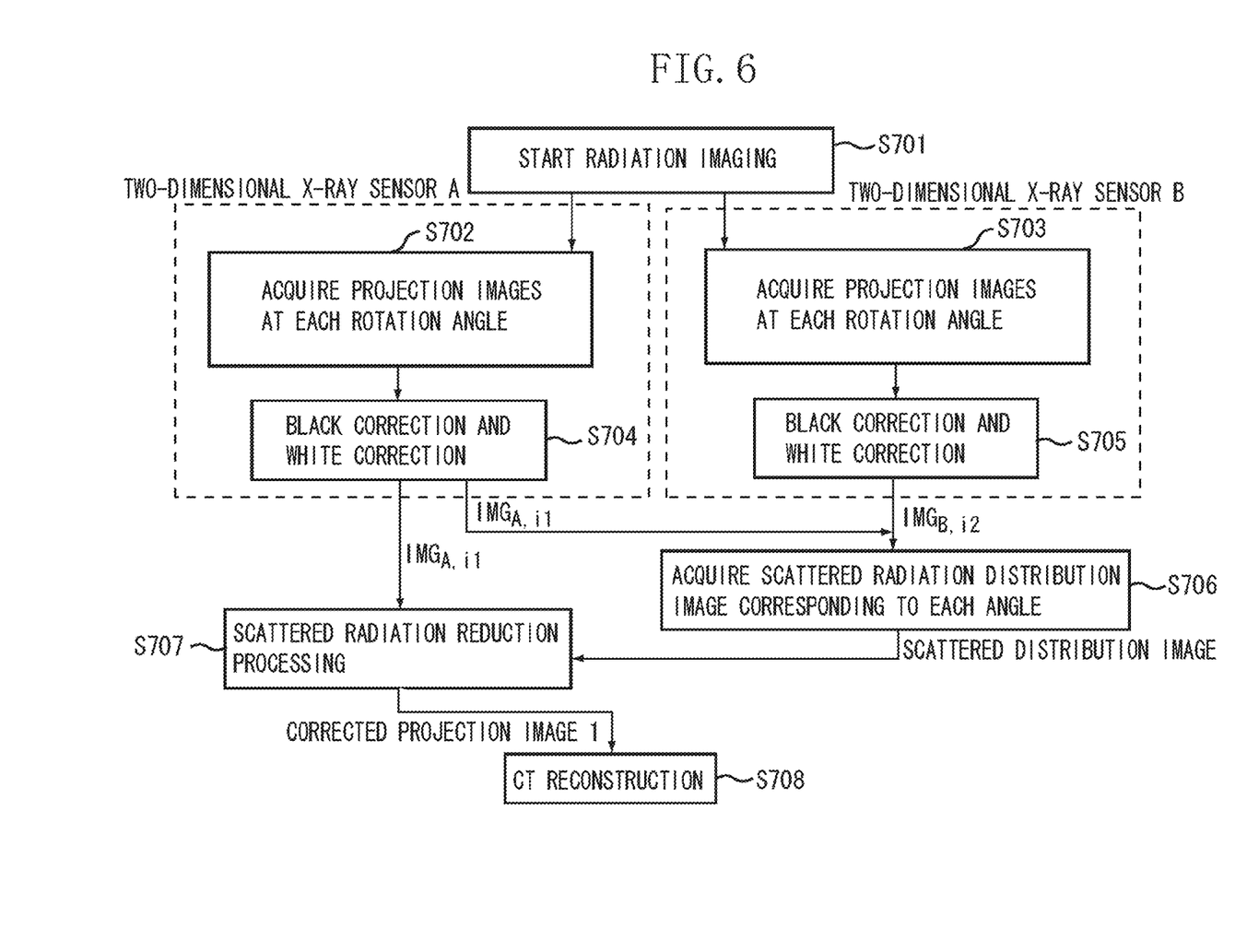
FIG. 6 is a flowchart illustrating an operation from imaging processing to CT reconstruction processing performed by a radiation imaging apparatus.

FIG. 6 is a flowchart of an operation from imaging processing to CT reconstruction processing performed by the radiation imaging apparatus according to the present exemplary embodiment.

In step S701, the CPU 1018 starts image processing in response to an imaging instruction from the operation unit 1017.

In steps S702 and S703, the two-dimensional radiation detection sensors A and B acquire images. Then, in steps S704 and S705, the white correction unit 1020 performs white correction processing on the acquired images, while the image processing unit 1022 performs black correction processing (dark current correction processing) on the acquired images.

In step S706, the scattered radiation correction unit 1014 acquires a scattered radiation distribution image (information on a scattered radiation distribution) based on each image subjected to the correction processing.

Then, in step S707, the scattered radiation correction unit 1014 performs scattered radiation reduction processing on the image detected by the two-dimensional radiation detection sensor A based on the scattered radiation distribution image acquired in step S706.

Then, in step S708, the image processing unit 1022 performs CT reconstruction processing. Thus, a tomographic image is obtained.

When a still image is captured, the image is blurred due to the influence of scattered radiation. On the other hand, a tomographic image before CT reconstruction, and the tomographic image after the reconstruction differ from each other in pixel value (commonly known as "CT value"). According to the present exemplary embodiment, the influence of the scattered radiation can be reduced.

In order to reduce scattered radiation, a general method for acquiring an image using a single two-dimensional radiation detection sensor provided with a grid may be possible. However, in this case, a possibility in which a dosage of a subject according to such a general method becomes larger than the dosage according to the present exemplary embodiment may be highly increased.

As compared with a case of using a two-dimensional radiation detection sensor provided with no grid (the two-dimensional radiation detection sensor A), it requires the intensity of radiation of 1.5 to 2 times intensity required by a general two-dimensional radiation detection sensor provided with a grid.

However, according to the present exemplary embodiment, the intensity of radiation required by the two-dimensional radiation detection sensor B provided with the grid 1008 is about 0.2 times that of radiation required by the two-dimensional radiation detection sensor A. Thus, the dosage of a subject according to the present exemplary embodiment is smaller than that according to the above general method.

When an image is acquired using a single two-dimensional radiation detection sensor provided with a grid, the intensity of radiation other than scattered radiation is reduced by the grid. The present exemplary embodiment can solve such a problem.

Figure 2:
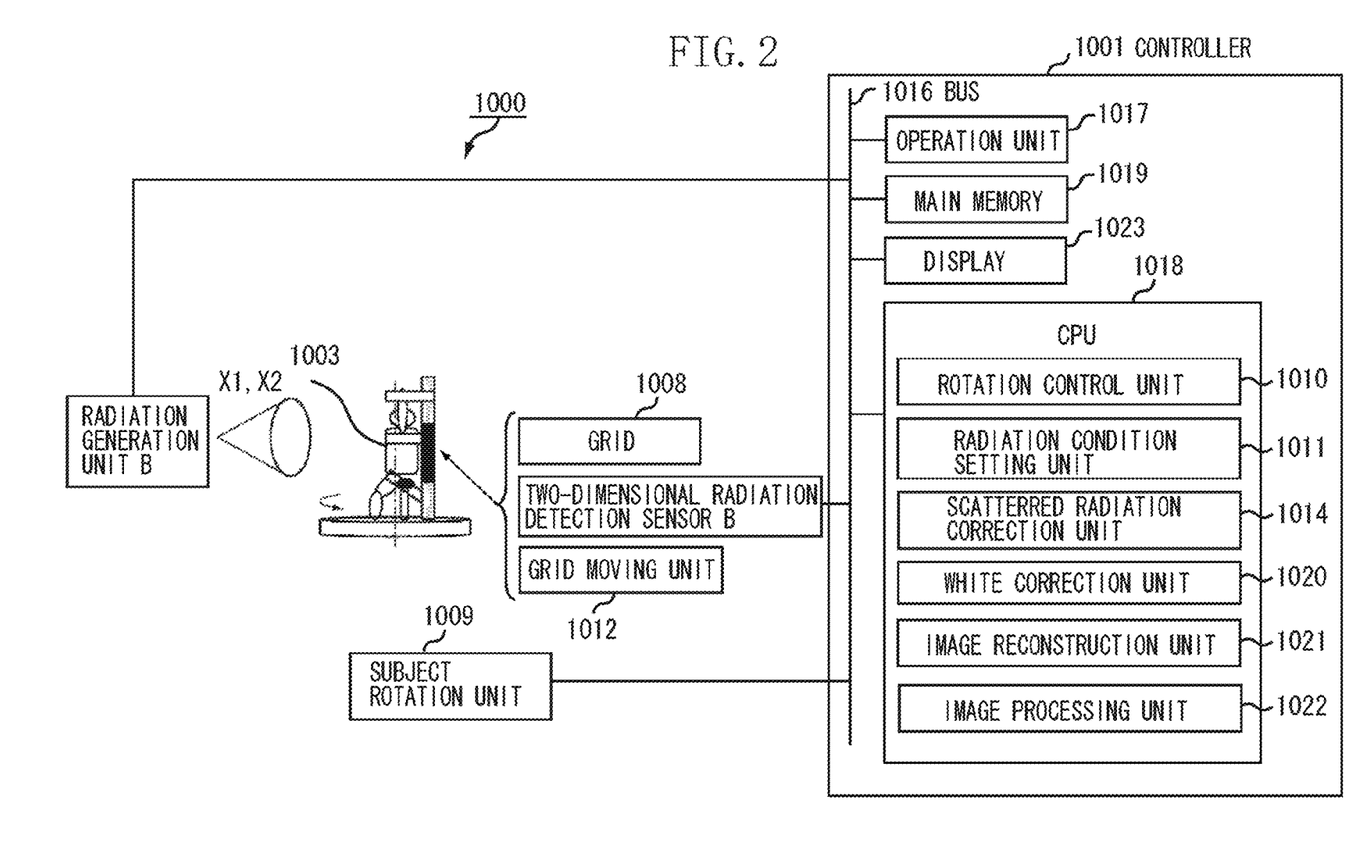
FIG. 2 illustrates a configuration of a radiation imaging apparatus according to a second exemplary embodiment of the present invention.

FIG. 2 illustrates a radiation imaging apparatus according to a second exemplary embodiment of the present invention. The second exemplary embodiment achieves the functions of the first exemplary embodiment using a pair of a radiation generation unit and a two-dimensional radiation detection sensor.

In principle, when image data is acquired at each rotation angle ranging from 0° to (180°+α) ("α" is a fan angle), image data sufficient for performing reconstruction to obtain a tomographic image can be obtained. Thus, according to the second exemplary embodiment, at each rotation angle ranging from 0° to (180°+α), imaging of the subject is performed in a state in which the grid 1008 is attached to the two-dimensional radiation sensor B. At that time, radiation generated from the radiation generation unit B is weak in intensity, and pixel addition processing is performed.

Next, the grid 1008 is moved by the grid moving unit 1012 from a radiation irradiation range (field). A method for moving the grid 1008 may be either to apply an external force to the grid 1008 using, e.g., a motor or to utilize a gravitational force. However, it is desirable to prevent, when the grid 1008 is moved, a mechanical vibration from being transmitted to the two-dimensional radiation detection sensor. This is because the two-dimensional radiation detection sensor is usually designed to include an electric circuit board and electrical wirings and contacts.

Then, in a state in which the grid 1008 is moved to outside the irradiation field, a radiation image is acquired by the two-dimensional radiation sensor B. At that time, radiation generated from the radiation generation unit B has intensity higher than that in a case where the grid is attached to the two-dimensional radiation sensor, and the interval to acquire images is longer than that.

According to the second exemplary embodiment, instead of the radiation detection sensors A and B used in the first exemplary embodiment, a single sensor is used. Thus, the radiation imaging apparatus can be reduced in size, though it is susceptible to the influence of a body movement.

A scattered radiation distribution image can be acquired at a time different from a time at which main imaging is performed. Thus, the present exemplary embodiment has an advantage in preventing scattered radiation to be generated by interaction between radiation generated by a radiation generation unit and radiation generated by another radiation generation unit at a subject.

Figure 8:
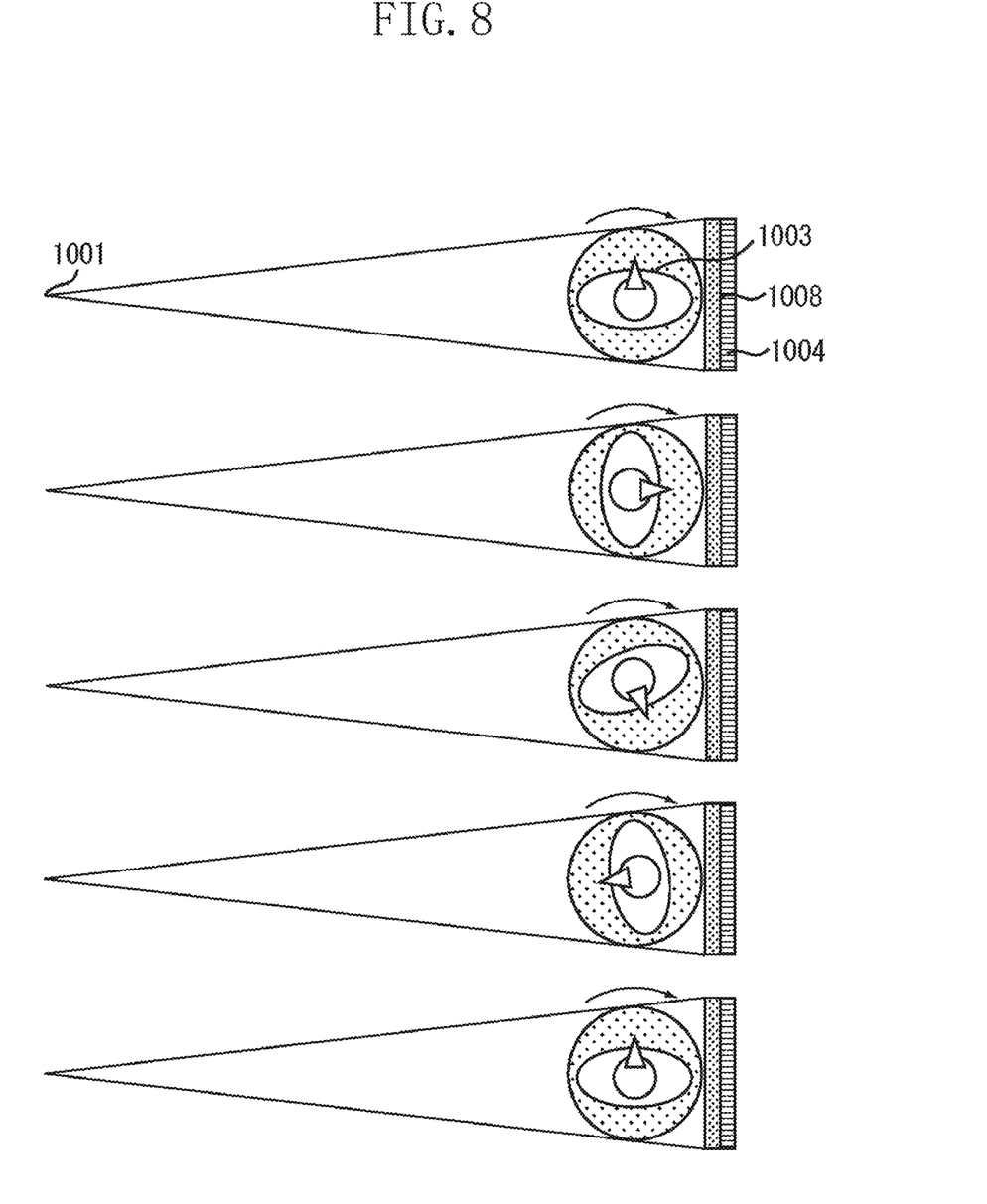
FIG. 8 illustrates an imaging state according to the second exemplary embodiment of the present invention.

FIG. 8 illustrates an imaging state according to the second exemplary embodiment of the present invention. Radiation generated from the radiation generation unit passes through a subject 1003 and reaches the two-dimensional radiation detection sensor B.

The grid 1008 is disposed in front of the two-dimensional radiation detection sensor B. When a rotation of the two-dimensional radiation detection sensor B of (180°+α), which is needed for reconstruction, is performed, the grid 1008 is moved to outside the radiation irradiation range by the grid moving unit 1012. While the grid 1008 is moved to outside the radiation irradiation range, no image is captured. Thus, the radiation generation unit B is controlled and set by the radiation condition setting unit 1011 or the like to stop the generation of radiation.

When the grid 1008 is moved to outside the radiation irradiation range, a radiation generation permission signal is turned on, and the generation of radiation is resumed. Then, upon completion of acquiring an image at each rotation angle ranging from 0 to (180°+α), the generation of radiation and the rotation operation of the subject rotation unit 1009 are stopped.

In the foregoing description of the present exemplary embodiment, it is assumed that what is called a "half scan" is performed. Thus, the maximum rotation angle is set to be (180°+α). However, the present invention can be applied to a case where what is called a "full scan" is performed so that the maximum rotation angle is 360°.

Figure 9:
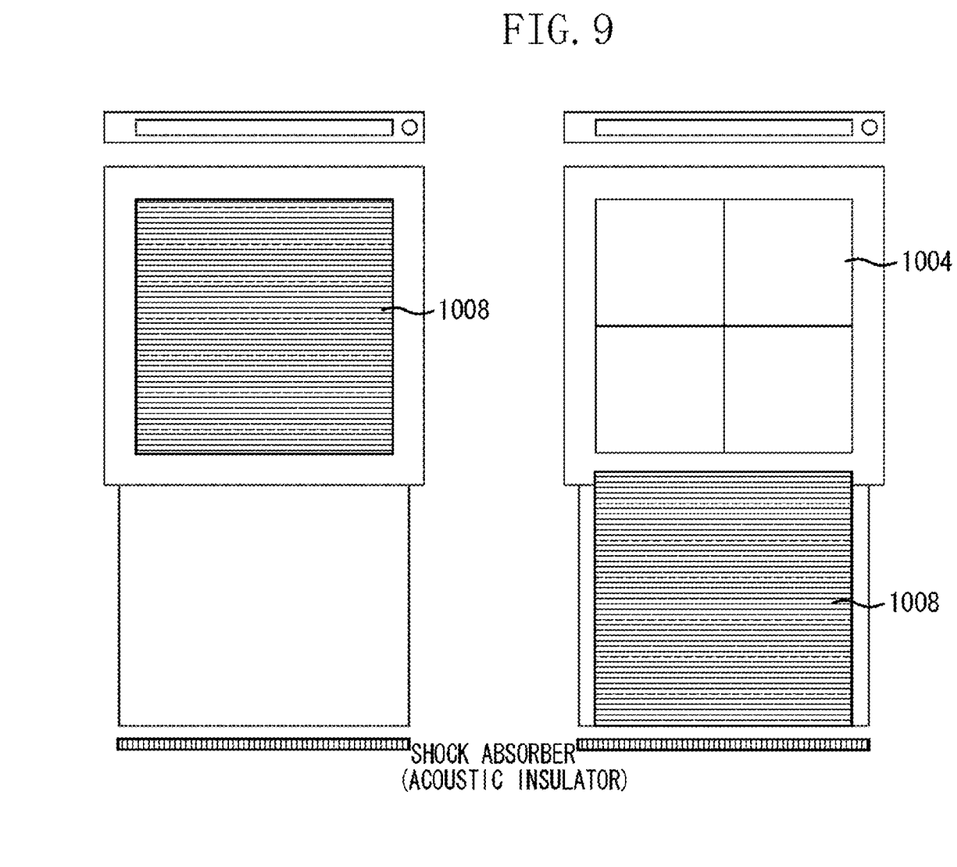
FIG. 9 illustrates an example of a grid moving operation of a grid moving unit.

FIG. 9 illustrates an example of a grid moving operation of the grid moving unit 1012. The grid 1008 is moved to outside the radiation irradiation range after the subject is rotated by the angle of (180°+α). The grid moving unit 1012 may move the grid 1008 by generating a force with a motor or the like. Alternatively, the grid moving unit 1012 may use a force such as a gravitational force.

FIG. 9 illustrates the example in which the grid 1108 is moved using an external force obtained by combining both the force generated by a motor and the gravitational force. In a case where the radiation irradiation range of the radiation imaging apparatus according to the present exemplary embodiment is, e.g., 43 centimeters (cm) long and 51 cm wide, a time taken to move the grid 1008 by 43 cm only using the gravitational force is about 0.3 seconds ($\approx(2\times0.43/9.8)^{1/2}$).

This time is negligibly short for the apparatus, because the apparatus takes 2.5 seconds to rotate the subject a half rotation. However, the grid should be moved while vibrations and impact are suppressed. Thus, it is desirable that some acoustic insulator or shock absorber is provided at a scattered radiation reduction member (grid) 1008 or at a portion to which the scattered radiation reduction member 1008 is fixed.

Figure 3:
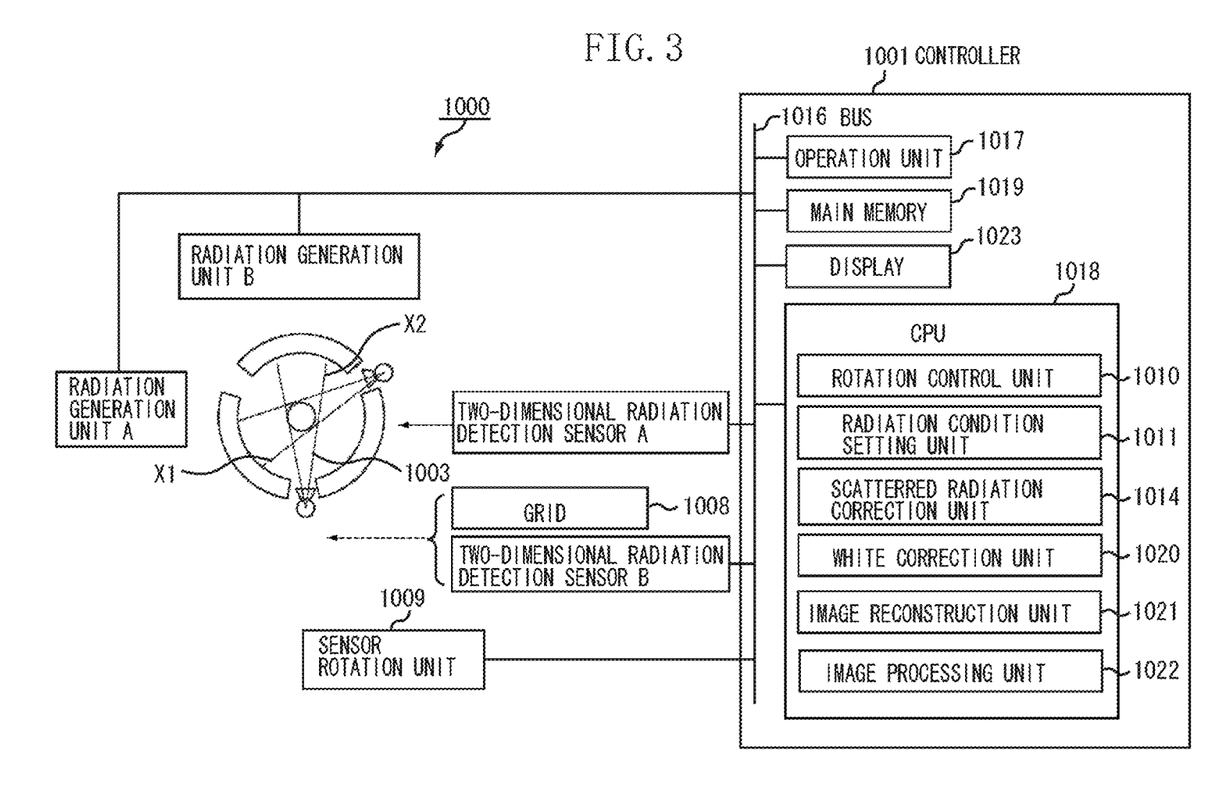
FIG. 3 illustrates a configuration of a radiation imaging apparatus according to a third exemplary embodiment of the present invention.

FIG. 3 illustrates a radiation imaging apparatus 1000 according to a third exemplary embodiment to which the present invention can be applied.

In the third exemplary embodiment, an example using a gantry type CT imaging apparatus is described. The third exemplary embodiment differs from the first and second exemplary embodiments in that the radiation generation units A and B, and the radiation detection sensors A and B are rotated around a subject 1003 while an angle of 180° between the radiation generation unit A and B, and the radiation detection sensors A and B is maintained respectively.

Because the radiation imaging apparatus is a gantry type CT imaging apparatus, usually, imaging can be performed while the subject 1003 lies on a bed. Processing performed on each of images obtained from the radiation detection sensors is substantially similar to that performed in the first exemplary embodiment. That is, the scattered radiation correction is performed on the captured images by a scattered radiation correction unit 1014.

According to the third exemplary embodiment, it is desirable that the distance between the subject 1003 and each of the radiation detection sensors A and B is, e.g., 70 cm or more. An amount of radiation that is generated by the interaction between radiation generated from one radiation generation unit and radiation generated from the other radiation generation unit, which is detected by each radiation detection sensor, is reduced due to a Greodel effect, with increase in the distance therebetween.

Hereinafter, a fourth exemplary embodiment is described, in which scattered reduction processing is performed as reconstruction post-processing.

Figure 7:
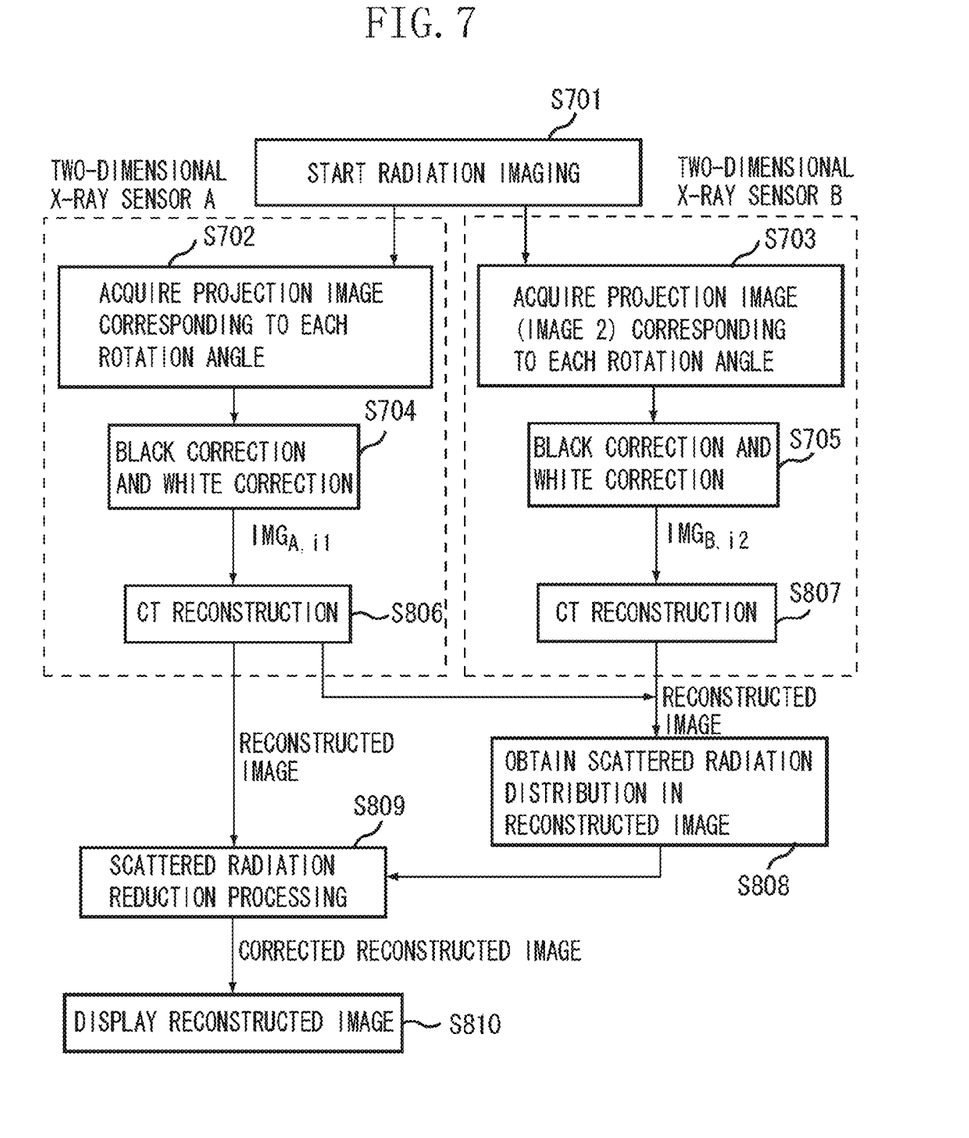
FIG. 7 is a flowchart illustrating another operation from imaging processing to CT reconstruction processing performed in a radiation imaging apparatus.

FIG. 7 is a flowchart illustrating an operation from imaging processing to CT reconstruction processing performed by the radiation imaging apparatus according to the fourth exemplary embodiment.

Processing performed in steps S701 through S705 illustrated in FIG. 7 is the same as that performed in steps S701 through S705 illustrated in FIG. 6. In steps S806 and S807, the image reconstruction unit 1021 obtains two reconstructed images based on the images acquired from the two-dimensional radiation sensors A and B, respectively.

In step S808, the scattered radiation correction unit 1014 obtains a scattered radiation distribution in each reconstructed image using the two reconstructed images. Each reconstructed image is a three-dimensional voxel image represented by, e.g., 512×512×512 voxels.

A reconstructed image (first reconstructed image) reconstructed based on the image acquired from the two-dimensional radiation sensor A includes scattered radiation, because the image is obtained by the two-dimensional radiation detection sensor that is not provided with the grid 1008.

Consequently, each pixel value, i.e., each CT value lacks in accuracy. In other words, each CT value is quite different from a value calculated using attenuation coefficients of materials constituting the subject.

In addition, an in-plane distribution may be generated in the CT value, so that shading may occur in a reconstructed image. A reconstructed image may be blurred due to scattered radiation, so that resolution is reduced. In order to process the blurred image, a scattered radiation distribution is obtained in the reconstructed voxel image.

More specifically, a scattered radiation approximation reconstructed image is obtained by subtracting a reconstructed image, which is subjected to reconstruction processing (second reconstruction processing) based on an image acquired from the two-dimensional radiation sensor B, from a reconstructed image reconstructed based on an image acquired from the two-dimensional radiation sensor A.

In step S809, a reconstructed image reduced in the influence of scattered radiation is obtained by subtracting the scattered radiation approximation reconstructed image, which is obtained in step S808, from the reconstructed image reconstructed based on the image that is acquired from the two-dimensional radiation sensor B.

While the present invention has been described with reference to exemplary embodiments, it is to be understood that the invention is not limited to the disclosed exemplary embodiments. The scope of the following claims is to be accorded the broadest interpretation so as to encompass all modifications, equivalent structures, and functions.

This application claims priority from Japanese Patent Application No. 2008-283309 filed Nov. 4, 2008, which is hereby incorporated by reference herein in its entirety.

What is claimed is:

1. A radiation imaging apparatus comprising:
   a first radiation detection sensor configured to detect radiation irradiated from a first radiation generation unit via no grid;
   a second radiation detection sensor configured to detect radiation irradiated from a second radiation generation unit via a grid;
   a rotation unit configured to rotate each of the first radiation detection sensor and the second radiation detection sensor relative to a subject;
   a correction unit configured to acquire information on a scattered radiation distribution based on images respectively obtained from the first radiation detection sensor and the second radiation detection sensor at each rotation angle preliminarily determined by the rotation unit and to correct the image obtained from the second radiation detection sensor based on the information on the scattered radiation distribution so as to reduce influence of scattered radiation thereon; and
   a reconstruction unit configured to perform reconstruction processing based on the image corrected by the correction unit.

2. The radiation imaging apparatus according to claim 1, further comprising a control unit configured to control the first radiation detection sensor and the second radiation detection sensor so that the number of images obtained from the first radiation detection sensor is less than the number of images obtained from the second radiation detection sensor.

3. The radiation imaging apparatus according to claim 2, wherein the correction unit is configured to correct an image obtained from the second radiation detection sensor based on information relating a scattered radiation distribution obtained based on an image obtained from the first radiation detection sensor, which is imaged at a rotation angle close to a rotation angle corresponding to the image obtained from the second radiation detection sensor.

4. The radiation imaging apparatus according to claim 1, further comprising:
   a moving unit configured to move the grid to outside a range in which radiation is irradiated,
   wherein the first radiation detection sensor and the second radiation detection sensor are configured in a single radiation detection sensor, and the first radiation generation unit and the second radiation generation unit are configured in a single radiation generation unit.

5. The radiation imaging apparatus according to claim 1, further comprising a setting unit configured to set intensity of radiation irradiated from the second radiation generation unit to be lower than that of radiation irradiated from the first radiation generation unit.

6. A radiation imaging apparatus comprising:
   a first radiation detection sensor configured to detect radiation irradiated from a first radiation generation unit via no grid;
   a second radiation detection sensor configured to detect radiation irradiated from a second radiation generation unit via a grid;
   a rotation unit configured to rotate each of the first radiation detection sensor and the second radiation detection sensor relative to a subject;
   a first reconstruction processing unit configured to perform a reconstruction processing based on an image acquired at each determined angle from the first radiation detection sensor;
   a second reconstruction processing unit configured to perform a reconstruction processing based on an image acquired at each determined angle from the second radiation detection sensor; and
   a correction unit configured to acquire information on a scattered radiation distribution based on images obtained by the reconstruction processing performed by the first reconstruction processing unit and the second reconstruction processing unit, respectively, and to correct the image obtained by the reconstruction processing performed by the second reconstruction processing unit based on the information on the scattered radiation distribution so as to reduce influence of scattered radiation thereon.

7. A processing method for controlling a radiation imaging apparatus having a first radiation detection sensor configured to detect radiation irradiated from a first radiation generation unit via no grid, a second radiation detection sensor configured to detect radiation irradiated from a second radiation generation unit via a grid, and a rotation unit configured to rotate each of the first radiation detection sensor and the second radiation detection sensor relative to a subject, the processing method, the processing method comprising:
   acquiring information on a scattered radiation distribution based on images obtained at each rotation angle determined by the rotation unit from a first reconstruction processing unit and a second reconstruction processing unit, respectively;
   correcting the image obtained from the second radiation detection sensor based on the information on the scattered radiation distribution so as to reduce influence of scattered radiation thereon; and
   performing reconstruction processing based on the corrected image.

8. A non-transitory computer-readable storage medium containing computer-executable instructions for controlling a radiation imaging apparatus having a first radiation detection sensor configured to detect radiation irradiated from a first radiation generation unit via no grid, a second radiation detection sensor configured to detect radiation irradiated from a second radiation generation unit via a grid, and a rotation unit configured to rotate each of the first radiation detection sensor and the second radiation detection sensor relative to a subject, the processing method, the medium comprising:
   computer-executable instructions that acquire information on a scattered radiation distribution based on images obtained at each rotation angle determined by the rotation unit from the first reconstruction processing unit and the second reconstruction processing unit, respectively;
   computer-executable instructions that correct the image obtained from the second radiation detection sensor based on the information on the scattered radiation distribution so as to reduce influence of scattered radiation thereon; and
   computer-executable instructions that perform reconstruction processing based on the corrected image.

* * * * *